United States Patent [19]
Etes et al.

[11] 4,078,568
[45] Mar. 14, 1978

[54] PLASTIC COMPOSITION AND METHOD

[75] Inventors: Donald E. Etes; James D. Finch, both of Crystal Lake, Ill.

[73] Assignee: Northern Illinois Research, Inc., Wonder Lake, Ill.

[21] Appl. No.: 731,744

[22] Filed: Oct. 12, 1976

[51] Int. Cl.² ............................................. A61F 5/44
[52] U.S. Cl. .......................... 128/283; 128/DIG. 24; 128/155; 252/316; 424/25; 424/28
[58] Field of Search ............... 128/283, DIG. 24, 155; 424/25, 28; 252/316

[56] References Cited

U.S. PATENT DOCUMENTS

| | | | |
|---|---|---|---|
| 3,490,454 | 1/1970 | Goldfarb et al. | 424/25 X |
| 3,877,431 | 4/1975 | Kross | 128/283 |

*Primary Examiner*—Leland A. Sebastian
*Attorney, Agent, or Firm*—Emrich, Root, O'Keeffe & Lee

[57] ABSTRACT

A plastic composition prepared by the reaction of a non-ionic water soluble acrylic polyelectrolyte and a cationic water soluble acrylic polyelectrolyte with propylene glycol and incorporating or conducting the reaction in the presence of polyvinyl pyrrolidone with or without water. In one embodiment a plastic composition adapted for use in contact with the skin, especially in the form of a pad, seal or bandage is prepared by reacting a mixture of: (1) acrylamide-beta methacrylyloxyethyl trimethyl ammonium sulfate copolymer; (2) polyacrylamide; (3) propylene glycol; and (4) polyvinyl pyrrolidone. The plastic composition can contain glycerin in varying amounts to enhance the "feel" and flexibility of the final product. Water can be incorporated with the polyvinyl pyrrolidone to reduce the gel time and facilitate the molding process. Useful embodiments of the composition having the proper gel structure and adhesiveness for use as molded seals or pads in ostomy appliances and skin-covering pads incorporated in a bandage are disclosed.

26 Claims, 4 Drawing Figures

U.S. Patent  March 14, 1978  4,078,568
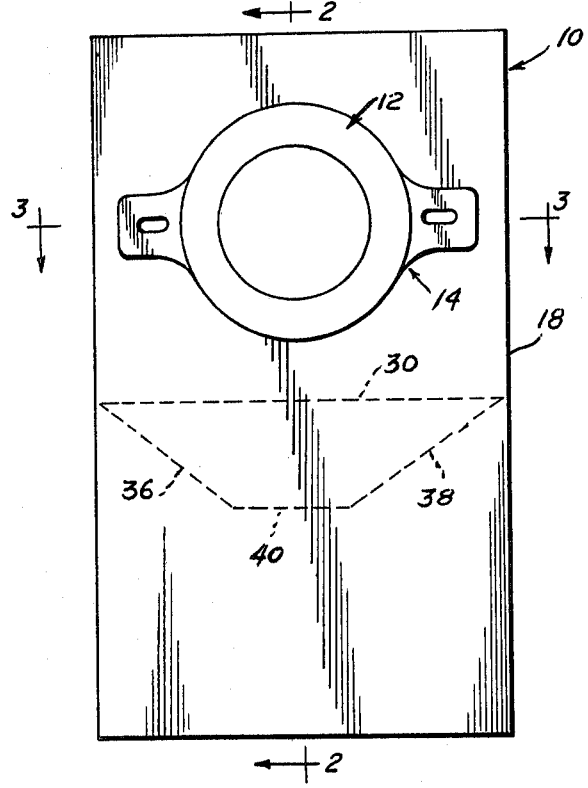
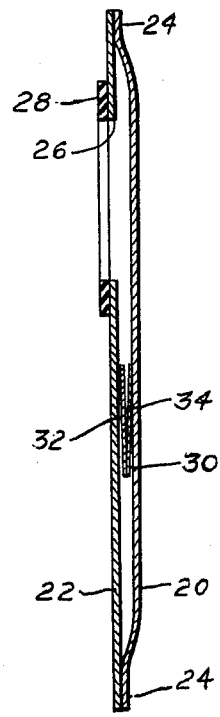
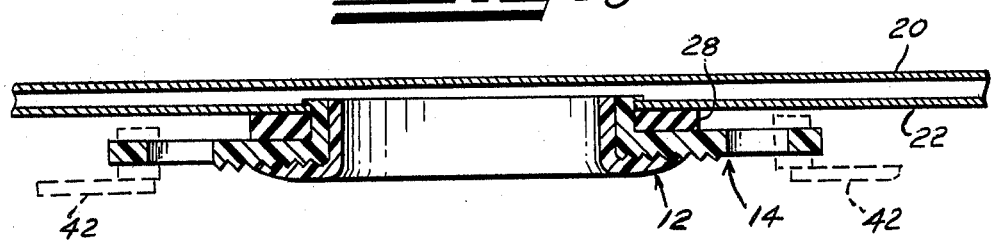
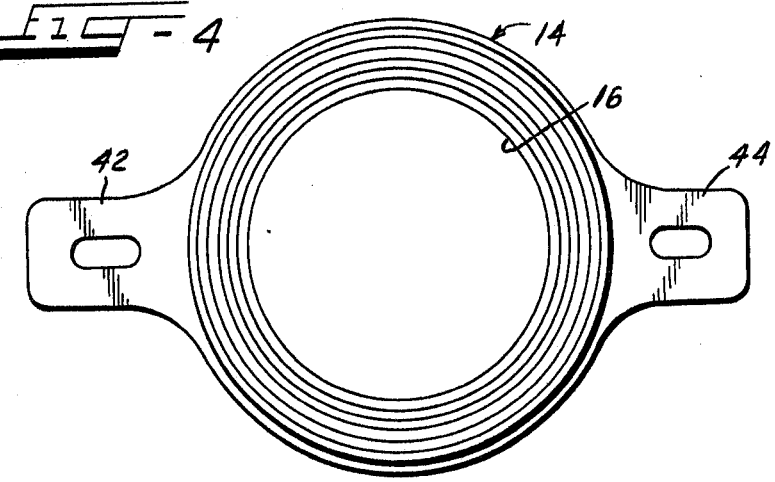

PLASTIC COMPOSITION AND METHOD

RELATED APPLICATIONS

U.S. applications Ser. No. 600,845, entitled OSTOMY APPLIANCES, and Ser. No. 600,847 (abandoned), entitled PLASTIC COMPOSITION MANUFACTURE THEORY, AND PAD FORMED THEREWITH, both filed on July 31, 1975 by one of the two inventors named herein are related insofar as the general subject matter is concerned.

BACKGROUND OF THE INVENTION

This invention relates to plastic compositions having particular adhesiveness, especially when wetted, that are particularly adapted for use in contact with the skin, to the manufacture thereof, and to articles formed therewith. More particularly, the invention relates to a plastic composition which may be formed as a pad for application to the skin, especially which may be formed as a sealing pad for an ostomy appliance and which also has other applications.

As is stated in said related application Ser. No. 600,847 certain abdominal surgery, such as colostomy, ileostomy, ureterostomy and the like, results in an opening in the abdominal wall from which extends a stoma for drainage of the interior of the abdominal cavity. A drainage appliance is employed to contain the waste discharged from the body, and it includes a face plate or ring surrounding the stoma and having a drainage pouch or bag mounted thereon to receive the waste. The applicance is supported on the wearer by a belt or strap. A sealing pad or gasket in the form of a ring is employed between the skin of the wearer and the face plate, to prevent leakage and keep the toxic fluids off of adjacent surfaces of the body, and to hold the appliance in place.

While several materials have been employed for forming the sealing pad of an ostomy appliance, pads based upon the inclusion of karaya powder, as disclosed in U.S. Pat. No. 3,302,647, are currently used. Karaya has certain disadvantages since it is a nutrient substance and capable of supporting the growth of micro-organisms, not only in use, but when contaminated in storage prior to use. Karaya compositions are lacking in cohesiveness, and therefore tend to break down in pieces, which may plug the valve employed at the bottom of the drainage pouch where employed in some instances. Also, it is difficult to form a sealing pad in a shape other than a flat ring. Karaya compositions become slippery when wet, so that a special adhesive may be needed to keep the sealing pad from sliding around and leaking. Karaya is not readily washed off the skin, but requires scraping for its removal.

In U.S. Pat. No. 3,640,741, Donald E. Etes one of the inventors named herein, has disclosed a plastic composition suitable for use in a sealing pad for an ostomy appliance, prepared by reacting carboxymethyl cellulose gum or alginate gum with a polyol to form a plastic gel. The carboxymethyl cellulose gum product does not support bacteria growth, and the alginate gum product supports only very little bacteria growth. It has been found that the preferred materials, however, become slippery when wet, and the materials may break up in pieces, which fall into the drainage pouch. Other characteristics of the compositions of the latter patent could be improved to advantage.

SUMMARY OF THE INVENTION

The invention relates to certain acrylic plastic compositions adapted for use in contact with the skin and to the manufacture thereof, such compositions being produced by reacting a mixture of: (1) about 20 to 100 parts by weight of acrylamide-beta methacrylyloxyethyltrimethylammonium methyl sulfate copolymer which characteristically contains about 10 to 40% by weight of the sulfate (MTMMS); (2) about 100 to 180 parts by weight of and acrylamide-sodium acrylate copolymer which characteristically contains a small amount of copolymerized sodium acrylate; (3) propylene glycol; and (4) polyvinyl pyrrolidone, the propylene glycol being present in an amount sufficient to form a thick gel and the polyvinyl pyrrolidone being present in an amount sufficient to add tackiness to the reacted mixture. The latter ingredient may be incorporated into the reaction mixture in the form of an aqueous solution. The invention also provides a self-adhesive pad adapted for application to the skin and formed of these ingredients.

For the sake of brevity, the respective acrylic polymer or resin ingredients are referred to at times as acrylamide-MTMMS copolymer and acrylamide-sodium acrylate copolymer. The polyvinyl pyrrolidone is a known commercial product generally referred to as PVP, (the preferred species being known as PVP-K90, supplied by GAF Corporation, Chemical Division).

Other examples of compositions will be disclosed to demonstrate various parameters of the invention as far as the end use is concerned, which may be outside the foregoing ranges, but which, nevertheless, have related utilities.

In one embodiment of the invention the compositions are prepared by a total of about 10 parts of a mixture comprising about 1.0 to 5.0 parts of acrylamide-MTMMS and about 5.0 to 9.0 parts of acrylamide-sodium acrylate copolymer are reacted with a stoichiometric equivalent, namely at least about 10 parts and preferably about 11 parts of the cross-linking agent, propylene glycol, and about 0.5 to 1.0 parts of PVP. The reaction mixture can, in addition, contain about 2.0 to 16 parts of glycerin and small amounts of water to enhance the softness and speed the gel time. In a preferred embodiment of the invention each 10 parts of said mixture of acrylics contains about 1.0 to 3.0 parts of acrylamide-MTMMS and about 7.0 to 9.0 parts of acrylamide-sodium acrylate, 10 to 11 parts of propylene glycol and 1.0 part of PVP with or without 9.0 parts of glycerin and with or without a small amount of water, ie, about 2.0 to 8% by weight.

The composition of the invention is especially adapted for use in forming a sealing pad for an ostomy appliance in the shape of a ring having a central opening for inserting a surgical stoma therethrough, the ring being adapted to be disposed between the skin and an ostomy appliance to provide a seal therebetween.

The new composition is advantageous for use in a sealing pad, and also for use in other applications in that it does not support the growth of micro-organisms, but is a non-nutrient material. Consequently, an article formed of the composition does not become contaminated by micro-organism growth during storage or when employed on the human body, especially when employed as a sealing ring adjacent to a stoma opening.

The composition has the unique properties of tackifying when wetted, and then remaining tacky and possessing good adhesive properties as it slowly dissolves.

Such properties are advantageous in a sealing pad for an ostomy appliance, in as much as they act to provide a continuing seal between the appliance and the skin, and the appliance is secured in place to minimize movement thereof around the stoma.

Another advantageous property of the new composition is its cohesiveness. This property enables the composition to be molded in preferred shapes without breaking apart in use. Rather, a sealing pad formed of the composition gradually dissolves in contact with body fluids or in contact with fluids normally present on the skin. The sealing pad lasts substantially longer than the above-decribed prior art sealing pads both in storage and in use. The new composition is relatively soft and resilient, minimizng discomfort to the wearer of an ostomy appliance. Material adhering to the skin or to clothing after use is easily removed by washing with soap and water.

Articles formed of the new composition have a long shelf life, in contrast to karaya products, which have but a limited shelf life and harden during storage.

The foregoing properties of the new composition render it useful in other pads applied to the skin. Thus, it is advantageous to incorporate in a bandage a pad formed of the composition, for contacting and covering an area of the skin. The pad is adapted to maintain cleanliness, in view of its lack of support for micro-organism growth. Its adhesiveness in relation to the skin serves to retain it in place. The pad both covers the area and affords protection against physical contacts therewith. When it is desired to change the bandage, the outer portion of the pad may be peeled off, to leave in place the portion which adheres to the skin, without disturbing the surface of the skin. When it is desired to remove the remainder of the pad, it may be washed off.

BRIEF DESCRIPTION OF THE DRAWINGS

An illustrative embodiment of the invention is shown in the drawings wherein:

FIG. 1 is a front elevational view of an ostomy appliance embodying the principles of the present invention;

FIG. 2 is a longitudinal sectional view taken substantially along the line 2—2 in FIG. 1;

FIG. 3 is a transverse sectional view taken substantially along the line 3—3 in FIG. 1; and FIG. 4 is a front elevational view of the face plate shown in FIGS. 1 and 3.

DESCRIPTION OF THE PREFERRED EMBODIMENTS

Referring to the drawing an ostomy appliance 10 of this invention normally includes an annular sealing ring 12, in this case formed of the plastic composition of this invention held in an annular face plate or retainer 14 formed of relatively stiff and hard material, such as a plastic, which retainer may be of any suitable type such as the retainer disclosed in said copending application Ser. No. 600,845, to include a flat disc-like annular body having a central opening 16 to receive the sealing ring 12.

The appliance 10 includes a receptacle in the form of a flexible bag 18, of flexible water-impervious material such as polyethylene or polypropylene film or sheet material having spaced walls 20 and 22, heat sealed at their edges, as indicated at 24, and including a corresponding opening 26, in one wall. The retainer 14 is suitably affixed within this opening and the sealing ring 12 is suitably engaged upon and within the retainer 14 as best indicated in FIG. 3.

A reinforcing member 28, of annular conforming configuration, can be interposed between the retainer 14 and the periphery of the opening 26. A valve member 30 is disposed in the bag 18 below the opening 26 for one-way flow of fluids downwardly therethrough and includes two flexible sheets 32 and 34 formed of polyethylene, for example, secured at their top edges, as by heat sealing to the inner surfaces of the walls 22 and 24 and also heat sealed along their sloping edges 36 and 38 to define an unsealed openable bottom edge 40.

The retainer 14 includes two radially outwardly projecting flanges 42 and 44 disposed on opposite sides thereof for the purpose of receiving an elastic belt 42 (shown in broken lines) which detachably secures the device to the body of the user. The appliance is constructed in this manner for arranging the body of the face plate adjacent to the body of the user, with a surgical stoma inserted through the opening in the plate and beyond the back panel, for drainage into the waste pouch.

The sealing pad or gasket composed of the composition of this invention is interposed between the face plate and the skin of the user surrounding the stoma. The sealing pad serves to contain the waste fluids, which are highly irritating to the skin and contain micro-organisms of the intestinal tract, and which give off offensive odors. Additionally, the sealing pad assists in retaining the appliance in place and makes the appliance more comfortable to wear.

The sealing pad of the invention is especially adapted for performing the foregoing functions. Owing to its composition, the pad may be cast in any desirable configuration, and it will retain its shape and not break apart in use.

The plastic compositions of the invention are semisolid gel products of the reaction of a mixture of two acrylic cationic and non-ionic polymers, and at least a stoichiometric amount of propylene glycol as a cross linking agent, the mixture also containing polyvinyl pyrrolidone (PVP). The compositions are formed with or without glycerine or water. The preferred cationic polymer is a copolymer of acrylamide and beta methacrylyloxyethyltrimethylammonium methyl sulfate (acrylamide-MTMMS). Preferably, the cationic copolymer contains about 10 to 40% by weight of MTMMS, corresponding to a molar proportion of about 3 to 12%, and the balance acrylamide. In a further preferred embodiment, the copolymer contains about 14 to 23% by weight of MTMMS, corresponding to a molar proportion of about 3 to 6%.

Illustrative cationic copolymers include the proprietary products known as Reten 210 and Reten 220 which are high molecular weight water-soluble polymers commercially available from Hercules Incorporated. The polymers have molecular weights on the order of about 5 to 10 million, and they are supplied as finely divided powders, having a screen analysis of 99% through Sieve No. 40 of the U.S. Sieve Series. The polymers have solution viscosities of 600 to 1,000 and as high as 1200 centipoises (viscosities determined in 1% aqueous solution at 25° C, Brookfield LVF, 30 rpm). The bulk density of these cationic polymers ranges from 37 to 53 lbs./cu.ft. and their cationic activity is provided by the quarternary MTMMS in combined form therewith. 1% solutions at 25° C exhibit a pH of 5 to 6. The polymer films (1.0 mil. thickness) show tensile strengths of 11,000 psi, an elongation of 2% and a modulus of 800,000 psi.

An illustrative commercially available nonionic acrylic polymer is the polyacrylamide product of Hercules Incorporated, commercially available under the proprietary name of Reten 420. This water-soluble polymer of acrylamide has an estimated copolymerized sodiium acrylate content resulting from hydrolysis of about 2 to 4% by weight and a molecular weight on the order of 5 to 10 million. The product is supplied as a powder, of which 99% passes through Sieve No. 20 of the U.S. Sieve Series. The polymer has a solution viscosity of 300 to 500 centipoises (1% aqueous solution at 25° C, Brookfield LVF, 60 rpm). The bulk density is about 42 lbs/cu.ft. and the 1% solution exhibits a pH of 7 to 8. The film properties are commensurate with the above-described Reten 210 polymer and the Reten 220 polymer.

It is preferred that polyvinyl pyrrolidone (PVP) also be included in the reaction mixture employed for making the new plastic composition. The PVP is employed in a proportion up to about 0.5 weight percent to 4.0 weight percent based on the total composition.

Propylene glycol is incorporated in the reaction mixture in an amount sufficient to form a semisolid gel. It is preferred that about 8.0 to 34 weight percent of the propylene glycol be present in the reaction mixture.

Reaction of the mixture of polymer or polymers and a gel-forming amount of propylene glycol occurs spontaneously at room temperature, or about 22° C, under substantially anhydrous conditions. As illustrated in the examples supra, a semisolid gel formed in this manner has the above-described properties which are advantageous for forming a pad for application to the skin. The composition may be formed into a desired shape by casting or injection molding.

A shaped composition formed by the inclusion of both acrylamide-MTMMS copolymer and polyacrylamide in the reaction mixture has a body and resiliency similar to silicone rubber. The composition is denser than the above-described prior materials employed for like purposes, affording more versatility in molding desired shapes. A shaped composition formed by the sole inclusion of the acrylamide-MTMMS copolymer, i.e., omitting the polyacrylamide, has less body and elasticity, and is more putty like. The latter composition also dissolves more rapidly.

The rate of gel formation may be regulated by cooling during the reaction, if desired. A more rigid, less resilient composition may be produced by conducting the reaction under higher temperature and pressure, for example, in an autoclave indirectly heated by steam at 15 p.s.i.g.

Medicaments, microbicides, and the like may be incorporated in the reaction mixture. In forming a bandage a reaction mixture is cast on or molded on to a backing sheet.

The following examples are furnished to illustrate the invention. It will be understood that the invention is not limited to the examples or to the materials, proportions, conditions, and procedures employed therein, which are merely illustrative.

An initial series of test compositions was prepared by mixing the acrylic polymers in powder form and then adding a polyol at room temperature. The materials were mixed for several minutes under substantially anhydrous conditions. The pH of the initial mass was determined to be about 5.5. The gel times and final pH were noted for each composition as shown in Table I.

TABLE I

| | | | TEST COMPOSITIONS | | | |
|---|---|---|---|---|---|---|
| NO. | RETEN 210 GMS. | RETEN 420 GMS. | POLYOL | (ML) | GEL FORMATION | pH |
| 1 | 6 | 54 | Glycerin | 240 | 120 min. | 6.0 |
| 2 | 60 | — | Glycerin | 240 | 60 min. | 6.0 |
| 3 | — | 60 | 1,3 butylene glycol | 240 | none | 5.5 |
| 4 | 6 | 54 | Triethylene glycol | 240 | none | 5.6 |
| 5 | — | 60 | Triethylene glycol | 240 | none | 5.6 |
| 6 | 6 | 54 | 1,3 butylene glycol | 240 | none | 5.5 |
| 7 | 60 | — | 1,3 butylene glycol | 240 | none | — |
| 8 | — | 60 | Glycerin | 240 | 60 min. | 6.0 |

Although a gel was formed with test composition No. 1, it was not thick enough and lacked the necessary tackiness for use in molding an ostomy ring. The gels formed with test compositions 2 and 8 did not thicken properly for molding, even after prolonged standing for 3 hours or more. No gels were formed wih composition nos. 3, 4, 5, 6 and 7, even after standing for 3 hours.

These test compositions further show that neither glycerine or 1,3 butylene glycol form a suitable gel with either Reten 210 acrylic polymer or Reten 420 acrylic polymer used alone or in admixture. It is to be observed that glycerin alone was particularly slow in reacting with the mixture of Reten 210 acrylic and Reten 420 acrylic, there being no substantial gel formation at the end of 120 minutes. Similarly, triethylene glycol is deficient in forming a suitble gel with either a mixture of these acrylics or Reten 420 acrylic used alone. By varying the formulations, different gel times were obtained but the gels were not suitable for forming an ostomy ring, though in each instance the pH did increase as the reaction reached its peak. Also, initial experiments with propylene glycol and a mixture of the Reten 210 and Reten 420 acrylics indicated a short reaction time to gel formation.

With this background the following Table II shows the formulations of compositions, which form gels having suitable properties for molding ostomy rings and the like using propylene glycol as the primary reactant.

TABLE II

| | POLYMER COMPOSITIONS | | | | | | | | | | | |
|---|---|---|---|---|---|---|---|---|---|---|---|---|
| | RETEN 210 | | RETEN 420 | | GLYCERIN | | PROPYLENE GLYCOL | | PVP | | $H_2O$ | |
| No. | gms. | wt% | gms. | wt% | gms. | wt% | gms. | wt% | gms. | wt% | gms. | wt% |
| 8-1 | 20 | 3.22 | 180 | 29.03 | 180 | 29.03 | 220 | 35.48 | 20 | 3.22 | 0 | 0 |
| 8-2 | 20 | 3.25 | 180 | 29.31 | 180 | 29.31 | 210 | 34.32 | 24 | 3.90 | 0 | 0 |

TABLE II-continued

| | POLYMER COMPOSITIONS | | | | | | | | | | | |
|---|---|---|---|---|---|---|---|---|---|---|---|---|
| | RETEN 210 | | RETEN 420 | | GLYCERIN | | PROPYLENE GLYCOL | | PVP | | $H_2O$ | |
| No. | gms. | wt% | gms. | wt% | gms. | wt% | gms. | wt% | gms. | wt% | gms. | wt% |
| 8-3 | 40 | 6.45 | 160 | 25.80 | 180 | 29.03 | 220 | 35.48 | 20 | 3.22 | 0 | 0 |
| 8-4 | 50 | 8.05 | 150 | 24.19 | 180 | 29.03 | 220 | 35.48 | 20 | 3.22 | 0 | 0 |
| 8-5 | 60 | 9.96 | 140 | 22.58 | 180 | 29.03 | 220 | 35.48 | 20 | 3.22 | 0 | 0 |
| 8-6 | 70 | 11.29 | 130 | 20.96 | 180 | 29.03 | 220 | 35.48 | 20 | 3.22 | 0 | 0 |
| 8-7 | 80 | 12.29 | 120 | 19.35 | 180 | 29.03 | 220 | 35.48 | 20 | 3.22 | 0 | 0 |
| 8-8 | 90 | 14.51 | 110 | 17.74 | 180 | 29.03 | 220 | 35.48 | 20 | 3.22 | 0 | 0 |
| 8-9 | 100 | 16.12 | 100 | 16.12 | 180 | 29.03 | 220 | 35.48 | 20 | 3.22 | 0 | 0 |
| 8-10 | 100 | 16.12 | 100 | 16.12 | 180 | 29.03 | 220 | 35.48 | 3.2 | 0.51 | 16.8 | 2.7 |
| 8-11 | 100 | 16.12 | 100 | 16.12 | 320 | 51.61 | 55 | 8.87 | 7.2 | 1.16 | 37.8 | 6.09 |
| 8-12 | 100 | 16.12 | 100 | 16.12 | 55 | 8.87 | 320 | 51.61 | 7.2 | 1.16 | 37.8 | 6.09 |

Each of the compositions of Table II exhibited an acceptable gel time and very good to fair skin adhesion properties when molded and brought into contact with the skin.

The gel compositions of Table II were each formulated into ostomy rings and subjected to the Dow Chemical Company test which measures the force in grams required to peel the rings from a polished steel surface. The results are shown in Table III.

TABLE III

| TEST FOR ADHESIVE PROPERTIES OF THE FORMULATIONS OF TABLE II: 8-1 THROUGH 8-12 | |
|---|---|
| COMPOSITION NO. | DOW CHEMICAL PEEL TEST |
| 8-1 | 1750 (gms) |
| 8-2 | 1700 (gms) |
| 8-3 | 1710 (gms) |
| 8-4 | 1705 (gms) |
| 8-5 | 1310 (gms) |
| 8-6 | 525 (gms) |
| 8-7 | 270 (gms) |
| 8-8 | 210 (gms) |
| 8-9 | 218 (gms) |
| 8-10 | 211 (gms) |
| 8-11 | 215 (gms) |
| 8-12 | 172 (gms) |

The weight ratio of Reten 210 acrylic polymer to Reten 420 acrylic polymer of about 20:80 provides the most favorable formulations. As this ratio approaches 35:65 the compositions begin to lose their adhesive properties, there is a tendency for the compositions to dry out and the ability to retain elasticity is lessened. The test results in Table III are the average of 24 samples for each test.

The addition of water to the formulations and adjustment of the ratio of glycerin to exceed the ratio of propylene glycol cause the formulations to become hydroscopic by as much as 51% total weitht. This is an indication of some instability. Centrifuging allows the separation of as much as 25% of the liquid from the mass. By heating the liquid phase so recovered the liquid was separated into water and glycerin in amounts which represented practically all of the water added initially and approximately 15% of the glycerin. This indicates that there is some cross-linking by means of the glycerin and that the water may be mechanically occluded in the plastic mass.

Also, it is apparent that a reversal of the proportions of glycerin and propylene did not change the gel or molding properties of the final products appreciably. A change in the ratio of the acrylic polymers by increasing the proportion of the Reten 210 acrylic tended to decrease the adhesion without affecting the gel time. The addition of water reduced the gel time by about 50%, though the adhesion became borderline, a result to be expected since the ratio of the acrylics was 1:1 in the compositions containing water. The presence of PVP in the compositions increased the tackiness but did not influence the gel time. In this regard experiments also established that compositions No. 1-4 of Table III when formulated without PVP meet the standards for molded products such as ostomy rings and exhibited Dow Peel Tests of 1600 to 1700 gms. Other plastic adhesive materials which are compatible with the polymer compositions of this invention may be used to augment the adhesive properties as desired.

The compositions exhibit minimal eye and primary skin irritation in testing in accordance with accepted test procedures as disclosed in said copending applications.

What is claimed is:

1. A process of making a plastic composition adapted for use in contact with the skin which comprises forming a mixture of a non-ionic water soluble polyacrylamide polyelectrolyte containing about 2% to 4% by weight of copolymerized sodium acrylate and a cationic water soluble polyelectrolyte acrylamide -beta methacrylyloxyethyltrimethylammonium methyl sulfate copolymer, and propylene glycol in an amount sufficient to form a gel.

2. A process as defined in claim 1 and wherein said copolymer contains about 10-40% by weight of beta methacrylyloxyethyltrimethylammonium methyl sulfate and the balance acrylamide.

3. A process as defined in claim 1 and wherein said propylene glycol is present in a weight proportion of about one part per part of said polymers.

4. A process as defined in claim 1 and wherein said copolymer contains about 14-23% by weight of beta methacrylyloxyethyltrimethylammonium methyl sulfate and the balance acrylamide, and said propylene glycol is present in a weight proportion of about one part per part of said polymers.

5. A process as defind in claim 1 and wherein said mixture contains about one part of glycerin per 1 to 4 parts of said polymers.

6. A process as defined in claim 1 and wherein said mixture contains about 1 part of polyvinyl pyrrolidone per 5 parts of said polymers.

7. A process as defined in claim 1 and wherein said polyacrylamide is present in a weight proportion of about 4 to 9 parts per part of said copolymer.

8. A process as defined in claim 7 and wherein said copolymer contains about 10-40% by weight of beta methacrylyloxyethyltrimethylammonium methyl sulfate and the balance acrylamide, and said propylene glycol is present in a weight proportion of about one part per part of said polymers.

9. A process as defined in claim 7 and wherein said copolymer contains about 14-23% by weight of beta methacrylyloxyethyltrimethylammonium methyl sulfate.

10. A plastic composition adapted for use in contact with the skin and produced by the process of claim 1.

11. A plastic composition adapted for use in contact with the skin and produced by the process of claim 7.

12. A pad adapted for application to the skin and formed of the composition of claim 10.

13. An annular sealing pad for an ostomy appliance formed of the composition of claim 10, having a central opening for inserting a surgical stoma therethrough, and being adapted to be disposed between the skin and an ostomy appliance to provide a seal therebetween.

14. A sealing pad as defined in claim 13 and having an annular disc-like body for disposition between the skin and the surface of an annular face plate in said appliance, and a rim integrally formed in one piece with said body around the inner periphery thereof and projecting outwardly therefrom through the face plate for disposition between the stoma and the face plate.

15. In a bandage for application to the skin, a pad formed of the composition of claim 10 arranged for contacting and covering an area of the skin.

16. A plastic composition formed by forming a mixture of:
a cationic copolymer of acrylamide and beta methacrylyloxyethyltrimethylammonium methyl sulfate;
a non-ionic polymer of acrylamide;
glycerin;
propylene glycol; and
polyvinyl pyrrolidone;
the ratio of said cationic copolymer and said non-ionic polymer being about 1 to 9 to 1 to 1, and the total amounts of glycerin and propylene glycol being in excess of the total amounts of said cationic and non-ionic polymers.

17. A plastic composition in accordance with claim 16 in which:
the ratio of the amounts of said cationic copolymer and said non-ionic polymer is about 1 to 9.

18. A plastic composition in accordance with claim 16 in which:
the ratio of the amounts of said cationic copolymer and said non-ionic polymer is about 1 to 1.

19. A plastic composition in accordance with clain 16 containing a small amount of water.

20. A plastic composition in accordance with claim 19 in which about 2 to 8% by weight of water based on the total composition.

21. A plastic composition in accordance with claim 16 in which:
said cationic copolymer of acrylamide is the copolymer of acrylamide and beta methacrylyloxyethyltrimethylammonium methyl sulfate containing about 10 to 40% by weight of said sulfate;
said non-ionic polymer of acrylamide is polyacrylamide containing about 2 to 4% by weight of copolymerized sodium acrylate.

22. A process of making a plastic composition in accordance with claim 1 in which about 7.0 to 9.0 parts of said nonionic water soluble polyacrylamide polyelectrolyte and about 1.0 to 3.0 parts of said cationic polyelectrolyte constituting a total of about 10 parts of said polyelectrolytes is mixed with about 10 to 11 parts of said propylene glycol, about 2 to 16 parts of glycerine and a small amount of water sufficient to facilitate gel formulation.

23. A process of making a plastic composition adapted for use in contact with the skin with comprises mixing an acrylic polyelectrolyte of the group consisting of nonionic water soluble polyacrylamide and a cationic water soluble acrylamide-beta methacrylyloxyethyltrimethylammonium methyl sulfate copolymer and mixtures thereof, with propylene glycol in an amount sufficient to form a gel.

24. A process in accordance with claim 23 in which about 1.0 to 5.0 parts of said nonionic water soluble polyacrylamide and about 5.0 to 9.0 parts of said cationic water soluble polyacrylamide is used, said mixture consisting a total of about 10 parts with at least about 10 parts of said propylene glycol.

25. A process in accordance with claim 24 in which said nonionic polyacrylamide contains about 2% to 4% by wt. of copolymerized sodium acrylate and said cationic polyacrylamide contains about 10to 40% by weight of said sulfate.

26. A process in accordance with claim 24 in which about 2.0 to 16 parts of glycerine per 10 parts of said mixture and a small amount of water are used.

* * * * *